(12) United States Patent
Rempe et al.

(10) Patent No.: US 11,219,869 B2
(45) Date of Patent: Jan. 11, 2022

(54) ENZYMATICALLY ACTIVE HIGH-FLUX SELECTIVELY GAS-PERMEABLE MEMBRANES FOR ENHANCED OIL RECOVERY AND CARBON CAPTURE

(71) Applicants: UNM RAINFOREST INNOVATIONS, Albuquerque, NM (US); NATIONAL TECHNOLOGY & ENGINEERING SOLUTIONS OF SANDIA, LLC, Albuquerque, NM (US)

(72) Inventors: Susan Lynne Rempe, Albuquerque, NM (US); Ying-Bing Jiang, Albuquerque, NM (US); Juan Vanegas, Albuquerque, NM (US); C. Jeffrey Brinker, Albuquerque, NM (US); Joseph L. Cecchi, Albuquerque, NM (US)

( * ) Notice: Subject to any disclaimer, the term of this patent is extended or adjusted under 35 U.S.C. 154(b) by 261 days.

(21) Appl. No.: 16/605,466

(22) PCT Filed: Apr. 27, 2018

(86) PCT No.: PCT/US2018/030029
§ 371 (c)(1),
(2) Date: Oct. 15, 2019

(87) PCT Pub. No.: WO2018/201098
PCT Pub. Date: Nov. 1, 2018

(65) Prior Publication Data
US 2020/0047132 A1 Feb. 13, 2020

Related U.S. Application Data

(60) Provisional application No. 62/490,802, filed on Apr. 27, 2017.

(51) Int. Cl.
*B01D 69/00* (2006.01)
*B01D 69/14* (2006.01)
(Continued)

(52) U.S. Cl.
CPC ......... *B01D 69/144* (2013.01); *B01D 53/228* (2013.01); *B01D 53/62* (2013.01);
(Continued)

(58) Field of Classification Search
CPC .......... B01D 2325/38; B01D 2255/804; B01D 53/62; B01D 69/144; B01D 2325/36;
(Continued)

(56) References Cited

U.S. PATENT DOCUMENTS 4,619,897 A 10/1986 Hato et al.
9,085,476 B2 * 7/2015 Sirkar .................. B01D 69/105
(Continued)

OTHER PUBLICATIONS

International Preliminary Report on Patentability in International Application No. PCT/US2018/030029 dated Nov. 7, 2019, 7 pages.
(Continued)

*Primary Examiner* — Anthony R Shumate
(74) *Attorney, Agent, or Firm* — MH2 Technology Law Group LLP

(57) ABSTRACT

A membrane structure for moving a gaseous object species from a first region having an object species first concentration, through the membrane structure, to a second region having an object species second concentration different from the first concentration is described. The membrane includes a supporting substrate having a plurality of pores therethrough, each of the plurality of pores defined by a first end, a second end and a surface of the supporting substrate extending between the first end and the second end as well as a nanoporous layer within the plurality of pores, wherein the nanoporous layer comprises a hydrophilic layer and a
(Continued)

hydrophobic layer. The membrane also includes a liquid transport medium within the hydrophilic layer. The liquid transport medium includes a liquideous permeation medium and at least one enzyme within the liquideous permeation medium. The at least one enzyme is reinforced by at least one stabilizing component.

37 Claims, 4 Drawing Sheets

(51) Int. Cl.
  *B01D 53/22* (2006.01)
  *B01D 53/62* (2006.01)
  *B01D 67/00* (2006.01)
  *B01D 69/10* (2006.01)
  *C12M 1/40* (2006.01)
  *C12M 1/12* (2006.01)
(52) U.S. Cl.
  CPC ......... *B01D 67/0037* (2013.01); *B01D 69/10* (2013.01); *C12M 21/18* (2013.01); *C12M 25/02* (2013.01); *B01D 2255/804* (2013.01); *B01D 2257/504* (2013.01); *B01D 2325/36* (2013.01); *B01D 2325/38* (2013.01)
(58) Field of Classification Search
  CPC ............ B01D 2257/504; B01D 53/228; B01D 69/10; C12M 21/18; C12M 25/02
  See application file for complete search history.

(56) References Cited

U.S. PATENT DOCUMENTS

| | | | |
|---|---|---|---|
| 9,242,210 B1 | 1/2016 | Jiang et al. | |
| 9,321,030 B2* | 4/2016 | Sukhishvili | B01J 20/3236 |
| 2003/0215941 A1* | 11/2003 | Campbell | G01N 33/5014 435/325 |
| 2009/0071896 A1* | 3/2009 | Mues | B01D 69/06 210/601 |
| 2010/0291045 A1* | 11/2010 | Jia | C12M 25/02 424/93.7 |
| 2012/0082839 A1* | 4/2012 | Ha | C04B 14/28 428/221 |
| 2013/0011332 A1* | 1/2013 | Boyden | A61K 9/0021 424/1.11 |
| 2013/0197420 A1 | 8/2013 | Fissell, IV et al. | |
| 2014/0093905 A1* | 4/2014 | Ingber | C12M 25/02 435/29 |
| 2014/0200511 A1* | 7/2014 | Boyden | A61K 9/1641 604/67 |
| 2014/0234946 A1* | 8/2014 | Constantz | B01D 53/78 435/266 |
| 2015/0307401 A1* | 10/2015 | Chen | C04B 28/02 106/18.11 |
| 2016/0313306 A1* | 10/2016 | Ingber | C12M 35/04 |
| 2020/0016548 A1* | 1/2020 | Spulber | B01D 69/144 |

OTHER PUBLICATIONS

PCT International Search Report and Written Opinion dated Nov. 29, 2018 in International Application No. PCT/US2018/030029, 7 Pages.

Lihong Bao et al., "Facilitated transport of CO2 across a liquid membrane: Comparing enzyme, amine, alkaline", Journal of Membrane Science, vol. 280, Issues 1-2, 2006, pp. 330-334. (Available Abstract Submitted).

* cited by examiner

ENZYMATICALLY ACTIVE HIGH-FLUX SELECTIVELY GAS-PERMEABLE MEMBRANES FOR ENHANCED OIL RECOVERY AND CARBON CAPTURE

This application is a U.S. National Phase application of PCT/US2018/030029 filed Nov. 29, 2017, which claims priority to provisional U.S. Patent Application Ser. No. 62/490,802 filed Apr. 27, 2017, the entireties of which are incorporated herein by reference.

PRIORITY

This application claims priority to provisional U.S. Patent Application Ser. No. 62/490,802 filed Apr. 28, 2017, the disclosure of which is herein incorporated by reference in its entirety.

GOVERNMENT RIGHTS

This invention was made with Government support under Contract No. DE-NA0003525 awarded by the United States Department of Energy/National Nuclear Security Administration. The Government has certain rights in the invention.

TECHNICAL FIELD

The present teachings relate generally to the field of selectively permeable membranes and, more particularly, to a selectively permeable membrane that uses enzyme catalysis or another catalytic method to accelerate the selective permeation process.

BACKGROUND

Carbon dioxide ($CO_2$) separation and capture is a global topic that is closely related to energy and the environment. For example: $CO_2$ capture from power plant flue gases would dramatically reduce greenhouse gases and the resulting deleterious effects; $CO_2$ extraction from low-grade natural gas is needed as an energy efficient technique to improve purity of the natural gas to pipeline standards; and captured $CO_2$ may be used for enhanced oil recovery (EOR) processes. $CO_2$ separation from gases and fluids also has many applications in the areas of medical science, chemical engineering, the petroleum industry and even food industries.

Most commercial $CO_2$ separation plants use a process referred to as "pressure swing adsorption" (PSA), which is based on chemical absorption with a monoethanolamine (MEA) solvent. PSA processes require large capital equipment investment and consume high amounts of energy needed for regeneration.

Membrane separation is a compact, energy-efficient, and inexpensive alternative to PSA. Some $CO_2$ membranes have been developed, which include porous $CO_2$ membranes based on physical separations such as Knudsen diffusion or molecular sieving, as well as dense $CO_2$ membranes (e.g. polymer membranes) based on chemical separation such as solubility and diffusion in the solid state. Porous membranes based on physical separations suffer from relatively poor selectivities. Additionally, physical separation depends strongly on the composition of other gases within the $CO_2$ mixture. Deficiencies of dense $CO_2$ membranes include a very low $CO_2$ flux across the membrane because of the small $CO_2$ solubility in the membrane and slow diffusion of $CO_2$ across the membrane. In general, most current $CO_2$ membrane technologies are not sufficiently efficient for practical applications.

An improved membrane for the effective separation of $CO_2$ from a gas or liquid, and its method of formation and use, would be desirable.

SUMMARY

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

In an embodiment there is a membrane structure for moving a gaseous object species from a first region having an object species first concentration, through the membrane structure, to a second region having an object species second concentration different from the first concentration. The membrane, comprising: a supporting substrate comprising a plurality of pores therethrough, each of the plurality of pores defined by a first end, a second end and a surface of the supporting substrate extending between the first end and the second end; a nanoporous layer within the plurality of pores, wherein the nanoporous layer comprises a hydrophilic layer, and a hydrophobic layer; and a liquid transport medium within the hydrophilic layer, wherein the liquid transport medium comprises a liquideous permeation medium and at least one enzyme within the liquideous permeation medium, wherein the at least one enzyme is reinforced by at least one stabilizing component.

In another embodiment there is method for moving an object species from a first region having an object species first concentration to a second region having an object species second concentration different from the first concentration using a membrane structure comprising a supporting substrate, wherein the method comprises: exposing a gas comprising the object species to a plurality of pores within a first side of the membrane structure, each of the plurality of pores defined by a first end, a second end and a surface of the supporting substrate extending between the first end and the second end; dissolving the object species within a liquid transport medium, wherein: the liquid transport medium is within a nanoporous layer that is within the plurality of pores; and the liquid transport medium comprises a liquideous permeation medium and at least one enzyme within the liquideous permeation medium, wherein the at least one enzyme is reinforced by at least one stabilizing component; after dissolving the object species within the liquid transport medium, moving the object species from the first side of the membrane structure to a second side of the membrane structure through the liquid transport medium; and releasing the object species from the liquid transport medium, out of the membrane structure, and into the second region.

In another embodiment there is a method for making a membrane structure, wherein the membrane structure is configured to move an object species from a first region having an object species first concentration at a first side of a membrane structure to a second region of having an object species second concentration different from the first concentration, the method comprising: providing a supporting substrate comprising a plurality of pores therethrough, each of the plurality of pores defined by a first end, a second end and a surface of the supporting substrate extending between the first end and the second end; coating the supporting substrate with a coating comprising at least one of a sol gel, a nanoporous polymer, and a nanoporous organic-inorganic composite to bridge the plurality of pores with the coating; drying the coating to form a hydrophobic nanoporous layer within the plurality of pores; treating the first side of the membrane structure to modify a first portion of the hydrophobic nanoporous layer to be a hydrophilic nanoporous layer; and exposing the nanoporous layer to a liquid transport medium wherein the liquid transport medium remains within the hydrophilic nanoporous layer and comprises a liquideous permeation medium and at least one enzyme within the liquideous permeation medium, reinforcing the at least one enzyme with at least one stabilizing component.

Some advantages of the embodiments will be set forth in part in the description which follows, and in part will be understood from the description, or may be learned by practice of the invention. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments of the present teachings and together with the description, serve to explain the principles of the disclosure. In the figures.

Figure 1:
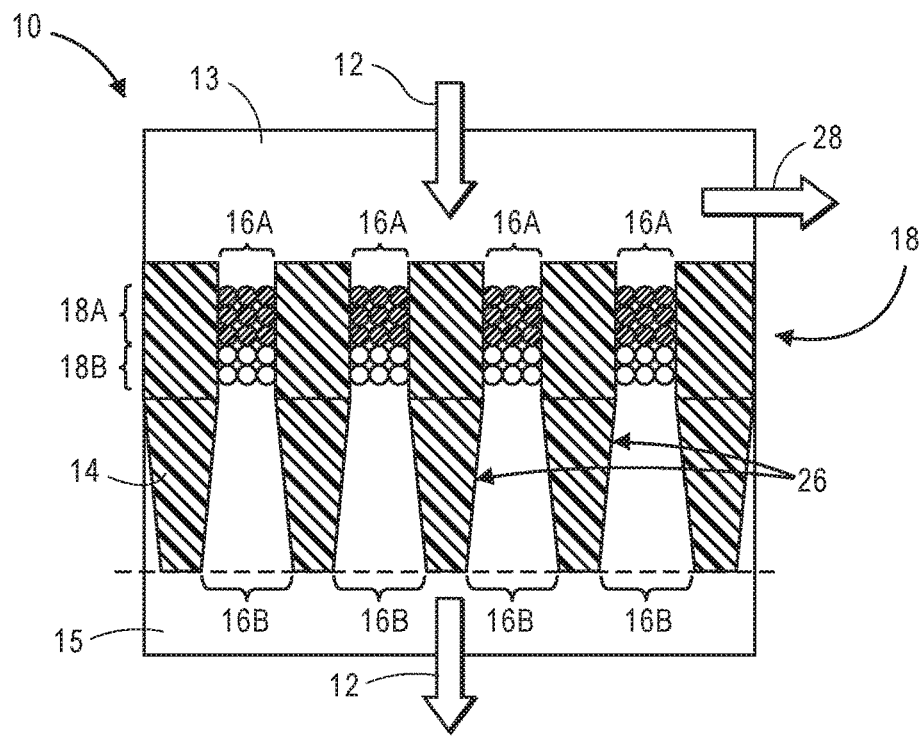
FIG. 1 is a schematic cross section depicting a membrane structure in accordance with an embodiment of the present teachings.

It should be noted that some details of the FIGS. have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same or like parts.

An embodiment of the present teachings includes a new technology for making an enzyme-catalyzed membrane that is effective for $CO_2$ separation, as well as the resulting membrane and its method of use.

For high selectivity, separation based on a chemical process (e.g., a catalytic process) instead of a physical process (e.g., based on diffusivity difference or size exclusion/molecular sieving) is preferred. For a membrane that utilizes a chemical process for separation, the separation process may involve the following steps: 1) an objective species such as $CO_2$ will interact with the membrane surface at the high concentration side of the membrane and dissolve in the liquideous permeation medium. An example would be $CO_2$ gas dissolved in an aqueous solution ($CO_2(g) \rightleftharpoons CO_2$ (aq)). 2) The dissolved objective species will be catalytically converted to dissolve into the membrane; 3) the dissolved species such as $CO_2$ will travel across the membrane thickness and arrive at the other side of the membrane, which is the collecting side to collect purified $CO_2$; 4) at the collecting side of the membrane, the dissolved species will be released from the membrane. The speeds of these steps are different and the overall transport speed depends most heavily on the slowest step.

Confining the enzyme and liquideous permeation media in a nano-structured membrane rather than a macroscopic structure confers at least three advantages. First, confinement in a pore with diameter slightly larger than the enzyme can result in enhanced enzyme stability and catalytic activity, as demonstrated for other enzymes (see, for example, Lei, et al., Characterization of Functionalized Nanoporous Supports for Protein Confinement, Nanotechnology, 17, 2006, 5531-5538; Lei, et al., Entrapping Enzyme in a Functionalized Nanoporous Support, J. American Chemical Society, Published on the Web 2002). Second, confinement in a pore with diameter slightly larger than the enzyme and width large enough to accommodate two or more enzymes can result in faster reaction rates due to assembly of an effective multi-enzyme complex and substrate channeling. In a multi-enzyme complex, the active sites that catalyze chemical reactions are in close proximity. Substrate channeling occurs when the chemical species produced by the first enzyme are also substrates for the nearby enzyme. The multi-enzyme configuration speeds chemical reactions by eliminating the time needed in bulk solution for free diffusion of substrates and enzymes to make random encounters. Third, confinement in a pore can result in a higher concentration of enzyme than can be achieved in bulk solutions. Such higher enzyme concentrations can result in higher rates of chemical reaction.

The carbonic anhydrase enzyme can be used to illustrate the advantages of a nanostructured membrane. The carbonic anhydrase enzyme is spherical, with diameter of 5 nm. A nano-structured pore ("nanopore") of diameter slightly larger than the enzyme (e.g. 6 nm) can stabilize the enzyme's structure, especially in the region of the active site. Enhanced structural stability means that the enzyme may retain catalytic activity for longer times and under a broader range of conditions (e.g., solution ionic strength, temperature). In addition to a nano-structured pore diameter, a pore width that accommodates two or more enzymes (e.g., 10 nm) can result in assembly of multiple carbonic anhydrases in close proximity and enhanced catalytic rates. Carbonic anhydrase enzymes catalyze $CO_2$ hydration or dehydration depending on which chemical species are present in excess. Excess $CO_2$ at the membrane surface results in enzyme catalysis of $CO_2$ hydration and formation of protons and $HCO_3^-$. The products of that first reaction diffuse down their concentration gradients only a short distance and then encounter the next enzyme. Excess protons and $HCO_3^-$ in the vicinity of the second enzyme are substrates for catalysis of $HCO_3^-$ dehydration. The second catalytic (dehydration) reaction forms $CO_2$ at the collecting end of the membrane. To summarize, nano-confinement of the enzyme and permeation media can result in a more stable enzyme structure that tolerates a wider range of solution conditions, faster transport of the object species through substrate channeling by multi-enzyme complexes, a higher concentration of enzyme and consequently, faster chemical reaction rates than achievable in bulk solutions. Further stabilization of the enzyme can be realized by reducing, minimizing or preventing protein unfolding. Accordingly, at least one enzyme may be stabilized by at least one stabilizing component that connects the at least one enzyme to a sidewall of the nanostructured pore and/or connects two or more enzymes together as at least one enzyme cluster.

An embodiment of the present teachings may therefore provide a membrane that transports an object species, such as a gaseous object species, at a broader range of temperatures, or at specific temperatures, not possible with conventional dry polymer membranes. For example, in an embodiment, the membrane structure 10 may provide sufficient transport of the object species at a broader temperature range of between about 0° C. and 60° C., or between about 40° C. and about 60° C., or at 0° C., 20° C., 40° C., or 60° C.

FIG. 1 is a schematic cross section depicting a membrane structure 10 according to an embodiment of the present teachings. The membrane structure 10 may be used to transport an object species 12 from a first region 13 having a first concentration of the object species to a second region 15 having a second concentration of the object species. In embodiments, the first concentration may be higher than or lower than the second concentration. The membrane structure 10 may include a supporting substrate 14 comprising a plurality of pores 16 (e.g., a plurality of nanopores). Each of the plurality of pores 16 may be defined by a first end 16A (e.g., an open end), a second end 16B (e.g., an open end) and a surface 26 of the supporting substrate 14 such as at least a portion of a surface 26 of the supporting substrate extending between the first end 16A and the second end 16B. The first end 16A of each pore 16 (i.e., an upper end 16A as depicted in the FIG. 1 orientation) may have a first diameter while a second end 16B of each pore (i.e., a lower end 16B as depicted in FIG. 1), wherein the first diameter is the same as, or different from, the second diameter. FIG. 1 further depicts a nanoporous layer 18 located within each of the plurality of pores 16. The nanoporous layer 18 may include a hydrophilic portion 18A ("hydrophilic layer") and a hydrophobic portion 18B ("hydrophobic layer"), and provides a nanoporous framework within the supporting substrate 14.

The surface 26 of the supporting substrate 14 (e.g., at a "pore surface portion" or "pore sidewall") may be modified. For example, the surface 26 may be modified to attain different properties than other portions of the supporting substrate. In an embodiment, the substrate surface may be modified to attain a hydrophilic property. In an implementation, the surface may be coated with a hydrophilic coating. In an implementation, the surface may be modified by a suitable surface modification process, for example, by atomic layer deposition (ALD), chemical vapor deposition, and the like. In an example, surface 26 may be modified with peptide chemistry by an atomic layer deposition process. The atomic layer deposition process may be thermal ALD or plasma ALD. The peptide chemistry can include one or more of a single amino acid, a chain of several connected amino acids, natural amino acids, unnatural amino acids, multiple types of amino acids, or combinations thereof. In an implementation the surface may be modified to have at least one stabilizing component formed thereon, such as anchored to the surface 26' as shown in FIG. 2B.

Figure 2A:
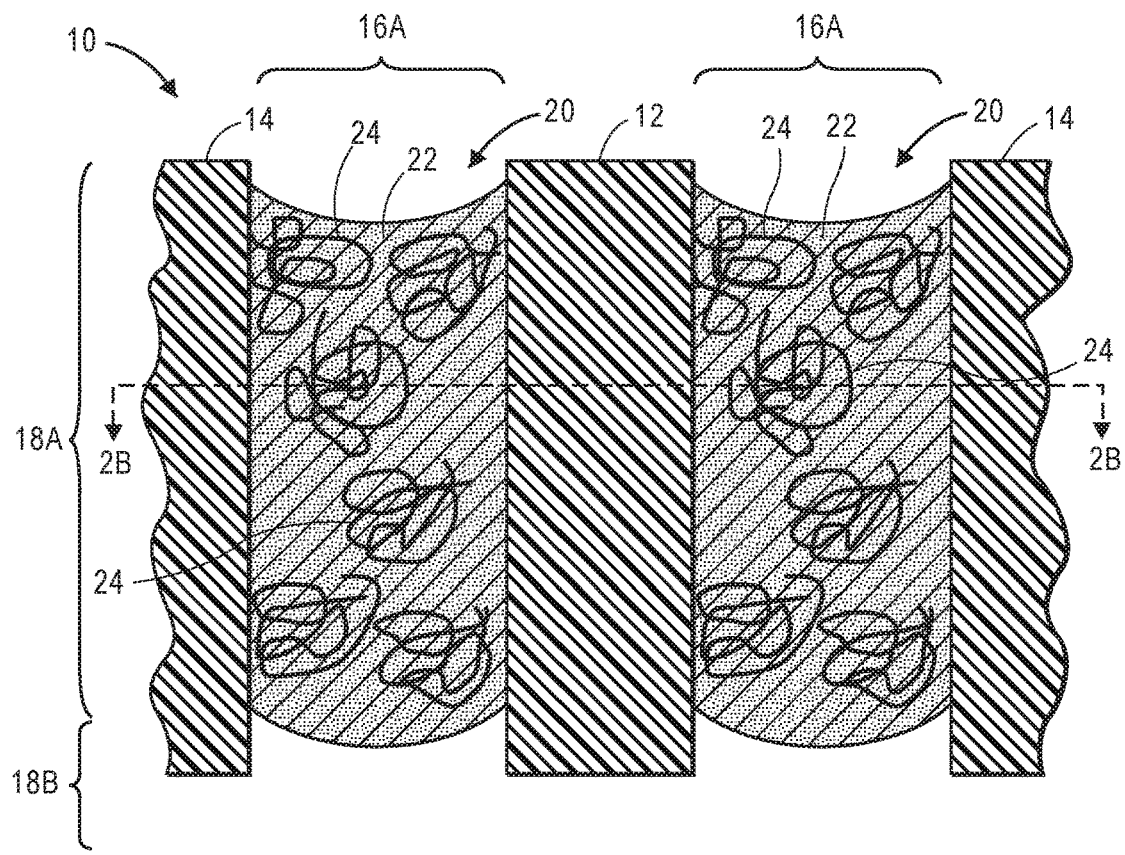
FIG. 2A is a magnified view of the FIG. 1 structure including a transport medium comprising at least one enzyme within a liquideous permeation medium and stabilized by a stabilizing component in accordance with an embodiment of the present teachings.
Figure 2B:
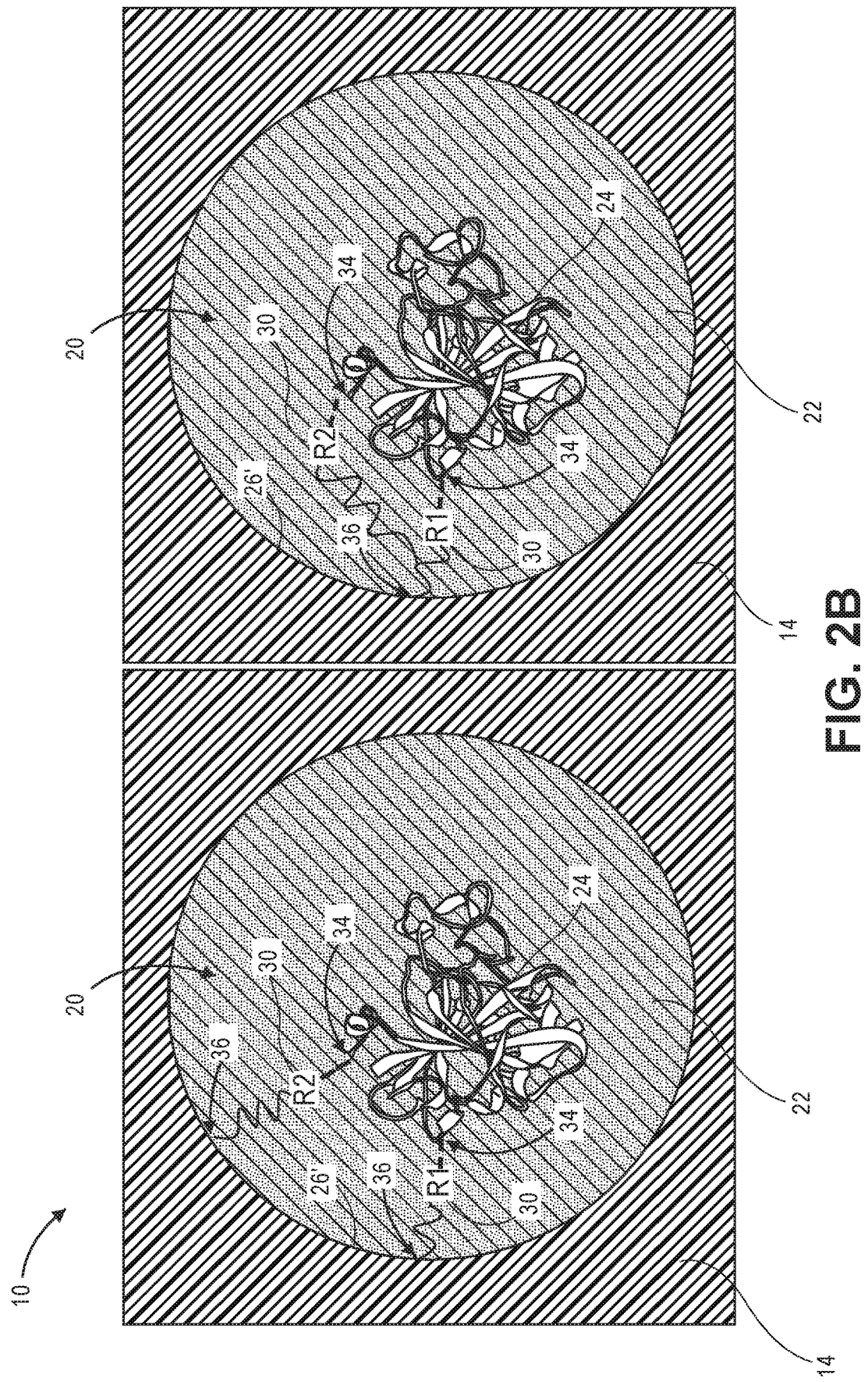
FIG. 2B is a magnified schematic cross section of FIG. 2A along cut-through line 2B-2B depicting the at least one enzyme within a liquideous permeation medium and stabilized by a stabilizing component in accordance with an embodiment of the present teachings.

FIG. 2A is a magnified view of the upper portion 16A of the membrane structure 10 of FIG. 1. For simplicity of depiction, FIG. 2A shows a magnification of two hydrophilic pores within the hydrophilic portion 18A. The membrane structure 10 may further include a liquid transport medium 20 formed within the hydrophilic portion 18A of the nanoporous layer 18 as depicted in FIGS. 2A-2B. Because the top portion is hydrophilic (i.e., hydrophilic portion 18A) and the bottom portion is hydrophobic (i.e., hydrophobic portion 18B), the liquid meniscus is depicted as concave on the top and convex on the bottom assuming the liquid medium to be water. The liquid transport medium 20 may include a liquideous permeation medium 22, all of which confines at least one enzyme 24 within the hydrophilic nanoporous region 16A×18A.

In an embodiment, the supporting substrate 14 may be an anodized porous alumina having a thickness of between about 5 nanometers (nm) and about 10 millimeters (mm), or between about 5 nm and about 100 micrometers (μm), or between about 1 μm and about 50 μm. The supporting substrate 14 may further have an average pore size of between about 10 nanometers (nm) and about 5,000 μm, for example about 20 nm. In an embodiment, the supporting substrate 14 may be an Anodisc™, available from Whatman plc. Various porous or permeable materials may be sufficient for the supporting substrate 14, including silica, other oxides or ceramics and glass, polymeric (polymer) materials, including ion etched polymer material, other inorganic materials, organic-inorganic composite materials, metallic (metal or metal alloy) materials, metallic composite materials (a metal and a non-metal), or a combination of two or more of these. In an embodiment, the disc may have a width/length or diameter of between about 0.5 centimeters (cm) and about 1000 cm, or another suitable size depending on the use. The disc may have a round, oval, square, rectangular, folded, pleated, corrugated shape, cylindrical shape or any number of other shapes depending on use. Materials from which the substrate can be made include one or more of polymer, ceramic, metal or glass.

At a first concentration side 13 of the membrane structure 10 (i.e., the top as depicted in FIG. 1), the pores 16 may have an average diameter of between about 2 nm and about 1000 nm, or between about 2 nm and about 10 nm, for example about 6 nm. At the second concentration side 15 of the membrane structure 10 (i.e., the bottom as depicted in FIG. 1), the pores 14 may have an average diameter of between about 2 nm and about 10 mm, or between about 10 nm and about 200 nm, for example about 150 nm, or between about 10 μm and about 10 mm. Thus the pores 16 within the supporting substrate 14 may or may not include a hierarchic porous structure along the thickness of the disc, and along a length of the pores 16, such that the pore opening at first end 16A at the top of the membrane structure 10 has a different average diameter than the pore opening at second end 16B at the bottom of the membrane structure 10. For the case of hierarchic porous structure, the average pore size at the first concentration side 13, for example the high concentration side, of the membrane structure 10 is smaller than the average pore size at the second concentration side 15, for example the low concentration side, of the membrane structure 10.

The nanoporous layer 18 may include a mesoporous or nanoporous silica layer embedded within the pores 16 of the supporting substrate 14. For purposes of this application, a "nanoporous" layer is a porous layer having an average pore size that is nanoporous or smaller (i.e., nanoporous or mesoporous), for example, having an average pore size of 100 nm or less. In an embodiment, an average size of the nanopores extending through the nanoporous layer may be between about 6 nm and about 8 nm in diameter. Various materials other than silica may be sufficient for the nanoporous layer 18, including a nanoporous polymeric material (i.e., a nanoporous polymer), nanoporous organic-inorganic composite, oxides, metals and metal alloys, carbon including graphene and graphene oxide, sulfides including molybdenum disulfide ($MoS_2$), and composites thereof. The nanoporous layer 18 may be much thinner than the supporting substrate 14 itself, for example between about 5 nm and 100 μm.

The liquideous permeation medium 22 that forms the liquid transport medium 20 may include (but is not limited to) water, water with salts, water with buffering species ("buffer") that assist in maintaining a constant pH, and combinations thereof, or other nonaqueous solutions.

The enzymes 24 within the liquid transport medium 20 including the liquideous permeation medium 22 may include (but is not limited to) carbonic anhydrases (CAs), or any other enzyme or other catalyst that catalyzes the dissolving or releasing process of the "object species" to be separated by this membrane.

Protein folding is critical for the function of the enzymes. The protein of an enzyme includes folds that optimizes its activity. Hydrogen bonding plays an important role in maintaining the folding structure, but hydrogen bonds are relatively weak as compared to, for example, covalent bonds. The increase of temperature, or the change of chemical environment such as pH or salt concentration, therefore, may result in deformation of the enzyme's shape or even cause the unfolding of the protein, resulting in denaturation of the protein and the loss of enzyme activity. Stabilization of the enzyme, for example, via its at least partial immobilization via confinement or stabilization via anchoring to a surface, or even stabilization via forming clusters of enzymes, can provide enhanced stabilization. In an embodiment, therefore, in addition to or separate from modifying of the local environment within the pores of porous layer 18, a surface chemistry of the porous layer 18, such as the surface 26 extending between first end 16A and second end 16B of the supporting substrate 14 as described above for FIG. 1, can be modified to further stabilize the enzymes 24. In an implementation, enzymes can be stabilized by at least one stabilizing component. In an implementation, the stabilizing of the enzymes can include attaching enzymes to other enzymes to form at least one enzyme cluster, and/or anchoring the enzyme(s) to the surface 26 extending between a first end and a second end of a pore. For example, the at least one stabilizing component can be physically or chemically bonded to a pore surface and chemically or physically bonded to the at least one enzyme. Accordingly, the enzyme(s) can be at least partially immobilized by the at least one stabilizing component to prevent the enzyme from undergoing protein unfolding, or at least reducing the occurrence thereof, thereby providing enhanced stabilization of the enzyme.

FIG. 2B is a magnified cross-sectional view of the upper portion at first end 16A of the membrane structure 10 of FIG. 1 taken at cut-through line 2B-2B of FIG. 2A. As shown in FIG. 2B, the at least one enzyme 24 is reinforced by at least one stabilizing component 30. In an example, the at least one stabilizing component 30 is anchored to the pore (e.g., nanopore) surface 26', which is illustrated as a portion of the surface 26 of supporting substrate 14 at a first location 36. In an example, another of the at least one stabilizing component 30 can be anchored to surface 26' at a second location 36'. The at least one stabilizing component can comprise a first functional group and a second functional group, wherein the first functional group is bonded to a first location of the enzyme and the second functional group is bonded to a second location of the enzyme. For example, as shown in FIG. 2B, the at least one stabilizing component 30 can comprise at least one functional group, R (e.g., R1 and/or R2), that is bonded to locations 34, 34' of the at least one enzyme 24. While not limited to any particular theory, it is believed that the at least one stabilizing component 30, anchored at location 36 to the pore at first location of the at least one stabilizing component and bonded to the enzyme at a second location, reinforces the enzyme structure, helps the enzyme maintain its natural shape (or the shape it attains upon being introduced into a one of the plurality of pores), and maintains the catalytic activity of the enzyme. The at least one stabilizing component 30 reinforces the enzyme structure, helps enzyme maintaining its natural shape and the activity. In an example, such as illustrated in the pore on the left-hand side of FIG. 2B, individual stabilizing components 30, 30 may comprise at least one respective functional group R1, R2. In an example, such as illustrated on the right-hand side of FIG. 2B, a single stabilizing component 30 may comprise at least two functional groups R1 and R2, that bond to a location 34 and 34 of the enzyme 24 structure. Additional configurations of the at least one stabilizing component are also possible. For example, in an embodiment the at least one stabilizing component comprises a single stabilizing component having a single functional group thereof bonded to the enzyme and anchored by a first location and a second location of the single stabilizing component to the pore surface (i.e., at least a portion of the surface of the supporting substrate) at a first location and second location, respectively. The stabilizing component can be incorporated with the coating of the modified hydrophilic surface of the nanopores. The stabilizing component can be applied to the coating of the modified hydrophilic surface by, for example, atomic layer deposition, dip coating, chemical vapor deposition or another other process that can be used to apply a chemical coating to the nanopore surface. The stabilizing component may be chemically attached by covalent bonds to the nanopore surface. The stabilizing component may form chemical bonds to the enzyme. The chemical bonds may comprise strong interactions like those from covalent bonds or ionic bonds. The stabilizing component may also stabilize the enzyme without forming strong bonds, but instead through weak bonds or secondary bonds like those from dipole-dipole interactions, dispersion interactions, and hydrogen bonding. In an implementation, the stabilizing component 30 can be anchored to the surface 26' by, for example, ionic and/or covalent bonding. For example, the stabilizing component 30 can be anchored to the surface 26' by, for example, chemical reaction between —OH groups on the pore surface 26' and reactive portions of the stabilizing component (e.g., a functional group such as —OCH4). Additionally, in another embodiment (not illustrated), the at least one enzyme may be at least partially surrounded by the at least one stabilizing component, for example, such that the at least one stabilizing component prohibits or limits the enzyme from substantially changing shape. The stabilizing component maintains the structure of the enzyme so as to minimize a loss in catalytic activity. In an embodiment, the stabilizing component maintains at least 90% of the catalytic activity. In an embodiment, the stabilizing component maintains at least 50% of the catalytic activity. In other embodiments, the stabilizing component may increase catalytic activity compared with activity achieved by enzymes in unconfined, bulk liquid solutions.

As described above, porous layer 18 comprises a plurality of pores, wherein each pore is defined by a first end, a second end and a surface extending between the first end and the second end. The geometry and size of pore features may prevent enzyme protein from unfolding and thereby improve enzyme stability. For an enzyme to be provided within a pore, such as at a hydrophilic portion 18A of the membrane 10, the enzyme molecule has to be small enough to enter through one of the ends of the nanopore. However, once an enzyme has been provided in the pore, it might otherwise easily escape the nanopore. In an implementation, pore surface chemistry can be modified so that the enzyme can be connected to a wall surface, for example, via forming a bond to the wall surface, as described above with respect to the stabilizing component-stabilized/reinforced enzyme in FIG. 2B. In an embodiment, several enzyme molecules may become bundled together via mechanical interaction or via chemical interaction such as by a stabilizing component. Such a bundle can be referred to as an enzyme cluster. An enzyme cluster can be formed such that it attains a size that is larger than one or both of the first end and the second end of the pore, thereby preventing the removal of the at least one enzyme from the pore.

Figure 2C:
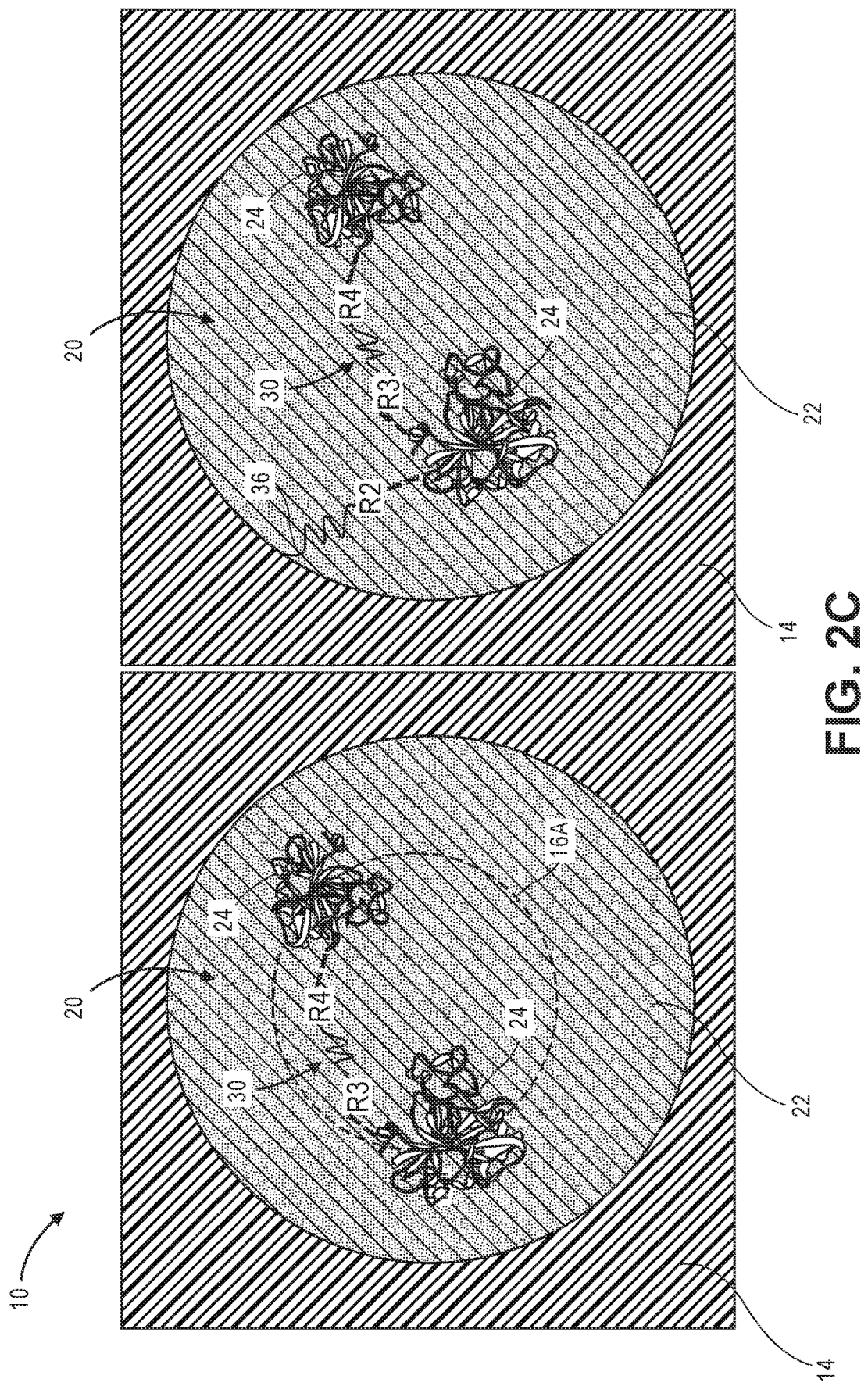
FIG. 2C provides the same view as FIG. 2B depicting the at least one enzyme within a liquideous permeation medium and stabilized by a stabilizing component wherein the enzyme and the stabilizing component are formed as at least one enzyme cluster in accordance with an embodiment of the present teachings.

As illustrated in FIG. 2C, after the at least one enzyme 24 is provided in the pore, stabilizing component comprising, for example, a molecule, such as a polymer, at least two functional groups, R3 and R4, is introduced into the nanopore. R3 and R4 may have bonding forces to corresponding sites of respective ones of two enzymes 24. The resulting enzyme cluster comprising a first enzyme 24, a second enzyme 24 and at least one stabilizing component 30 linking the first enzyme and the second enzyme, can comprise a size that is larger than an opening at first end 16A (dashed lines represent the size of the opening at end 16A as compared to the enzyme cluster). Due to this size mismatch, enzymes 24 are prevented from escaping from the pore. In an implementation, an enzyme cluster can be anchored at 36 to the pore surface 26' as shown in the right-hand side of FIG. 2C.

In an embodiment, the at least one stabilizing component 30 comprises surface chemistries for attachment to the enzyme. The stabilizing component can include one or more of ions, molecules, or a combination thereof, for example, one or more of a ligand, a polymer, or other organic material, or combinations thereof. In an implementation, the stabilizing component can comprise a molecular network, for example, at least one linear or branched polymer, or at least one cross-linkable polymer (e.g., at least two crosslinked polymers). The stabilizing component can include one or more organic functional groups (e.g., one or more of amines, carboxylic acids, hydroxyls, amides, aldehydes, thiols, sulfides, alkyls, or a combination thereof). The stabilizing component can comprise at least one cross-linking component including, for example, one or more polymeric units, amino acids, proteins, or combinations thereof. In an implementation, the stabilizing component comprises glutaraldehyde (a pentanedial, which polymerizes by aldol condensation reaction). At least one stabilizing component can also be added to the enzyme in solution to promote enzyme-enzyme attachment (i.e., enzyme cluster formation).

In an embodiment for forming the membrane structure 10, the disc used for the supporting substrate 14 may be coated with a coating including at least one of a sol-gel solution, a nanoporous polymer, or a nanoporous organic-inorganic composite. The coating may include a surfactant. The coating bridges the pores 16 within the supporting substrate 14 and forms a mesoporous or nanoporous layer 18, for example a nanoporous silica layer having a thickness of between about 5 nm and about 100 µm as depicted in FIG. 1. The nanoporous layer 18 (e.g., a nanoporous silica layer) may be formed, for example, using a process called "evaporation induced self-assembly" (see Brinker et al., Advanced Materials, V. 11, no. 7, p. 579, 1999). Due to capillarity, the sol-gel solution tends to remain within the narrower, upper portion of the pores 16A within the supporting substrate 14, and does not remain within the wider, lower portion of the pores at second end 16B after drying. The wider pore portions thereby remain generally free from the material that forms the nanoporous layer. Therefore, the smaller portions toward the first end 16A of the pores 16 at the top surface of the supporting substrate 14 (referring to the orientation of FIGS. 1 and 2) can be with nanoporous silica while the larger portions toward the second end 16B of the pores 16 at the bottom surface of the supporting substrate 14 can generally remain unfilled by the nanoporous silica as depicted in FIG. 1.

After forming the nanoporous layer 18, the sample, for example the entire sample including pores 16A, 16B within the supporting substrate 14 and the pores within the nanoporous layer 18, may be treated with a hydrophobic surface treatment, such as an exposure of exposed surfaces to hexamethyldisiloxane (HMDS). This renders both the exposed porous surface of the nanoporous layer 18 and the surface 26 of the supporting substrate 14 hydrophobic. In another embodiment, various structures may be inherently hydrophobic such that this hydrophobic surface treatment is optional.

Subsequently, the top surface of the supporting substrate 14 and nanoporous layer 18 were irradiated with an oxygen plasma and ozone. In an embodiment, irradiation may include an exposure to an oxygen plasma for a duration of between about 1 second and about 60 seconds, for example about 5 seconds. The oxygen plasma may be generated by argon (Ar) and molecular oxygen ($O_2$) in a ratio of between about 0:1 and about 100:1, for example about 1:1. The surface treatment may be performed at a vacuum pressure of between about 20 mTorr and about 500 mTorr, for example about 150 mTorr, and a radiofrequency (RF) power of between about 20 Watts and about 300 Watts, for example about 60 Watts. The irradiation treatment resulted in a thin portion of the nanoporous layer 18 becoming highly hydrophilic, thereby forming the hydrophilic portion 18A. In an embodiment, the hydrophilic portion 18A may have a thickness of between about 2 nm and about 10 µm, or between about 2 nm and 1000 nm, or less than about 100 nm, or less than about 50 nm. Portion 18B of the nanoporous layer 18 remains hydrophobic. In an embodiment, hydrophobic portion 18B may have a thickness of between about 0 nm and about 5 mm.

After the irradiation treatment, the sample was soaked in a volume of the liquid transport medium 20, which included the liquideous permeation medium 22 and the enzyme 24. As most parts of the sample disc, including of the nanoporous layer 18 are inherently hydrophobic (e.g., the hydrophobic portion 18B) with only a thin top layer being hydrophilic (e.g., the hydrophilic portion 18A) through exposure to the plasma, the transport medium will remain only within the hydrophilic portion 18A of the pores (e.g., nanopores) in the nanoporous layer 18. The thickness of this liquideous membrane depends on the time and intensity for plasma and ozone irradiation. FIGS. 1 and 2 depict a schematic cross section of an enzyme-catalyzed membrane structure according to an embodiment of the present teachings.

The enzyme 24 can be reinforced/stabilized with at least one stabilizing component 30. In an implementation, enzyme 24 can be attached to the at least one stabilizing component 30 prior to loading or after loading of the liquid transport medium 20 in the hydrophilic portion 18A of the pores 18, for example, prior to or after exposing the pore layer 18 (e.g., nanoporous layer) to the liquid transport medium. In an implementation, the hydrophilic portion (i.e. active layer) of the membrane 10 can be loaded with the liquid transport medium 20 in which the enzyme is dissolved, by immersion in the liquid transport medium, spraying the liquid transport medium into the membrane, or exposing the membrane to a vaporized form of the liquid transport medium (e.g., the enzyme, stabilizing component and liquid transport medium can be made in vapor phase) to be taken up into the membrane by capillary condensation.

This membrane structure 10 has substantial advantages during separation of the object species 12, for example during interaction of the membrane surface on the first concentration side 13, transport of the object species 12 across the membrane structure 10, and release of the object species 12 at the second concentration side 15 as described below. The gas 28 without the object species 12, or with a lower concentration of the object species 12, remains on the first concentration side 13 of the membrane structure 10.

For movement of an object species 12 into the membrane 10, an object species such as $CO_2$ molecules from the feeding mixture exterior to the membrane structure at the concentration side 13 are dissolved into the transport medium 20 that includes the liquideous permeation medium 22 and the enzyme 24 within the nanoporous layer 18. A liquideous permeation medium 22 by itself can dissolve $CO_2$ much faster than solideous polymers. In addition, this dissolving process can be further accelerated by the $CO_2$ enzyme 24 embedded in the membrane structure by $10^5$ times (see, for example, J. Gutknecht et al., Journal of General Physiology, V. 69, p. 779, 1977). Dissolution involves hydration ($CO_2$(aq)) and chemical reaction with a deprotonated water molecule ($OH^-$) to form highly soluble species: bicarbonate ($HCO_3^-$) and a proton ($H^+$). Because the membrane structure 10 includes the liquideous permeation medium 22, step one for this membrane structure 10 is expected to be much faster than conventional polymer membranes.

Figure 4:
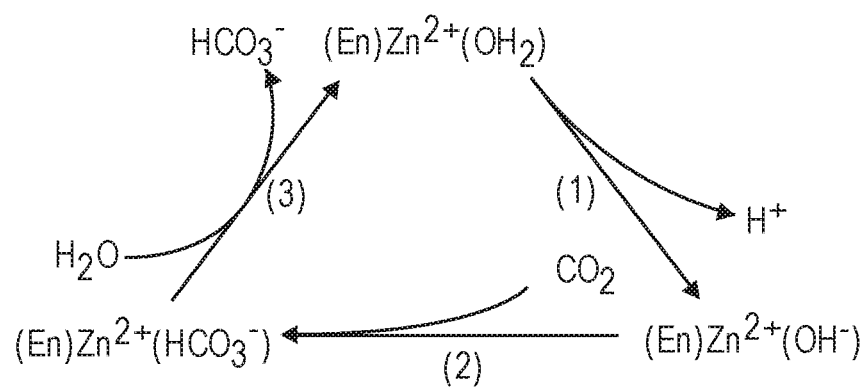
FIG. 4 depicts various reactions involved with a specific exemplary embodiment of the present teachings.

Next, the $CO_2$ 12 dissolved within the transport medium 20 crosses the thickness of the membrane. The transport medium 20 includes the permeation medium 22 in liquid phase. In general, the diffusion of the object species 12 through liquid phase is much faster than the diffusion of the object species through a solid phase alone. For at least this reason, the dissolved $CO_2$ can travel from one side of the membrane to the other side much faster than it can travel through a conventional polymer membrane. Further, the movement of the object species across the membrane structure 10 is a catalyzed transport process, because an enzyme accelerates $CO_2$ dissolution into and release from the transport media. In particular, the carbonic anhydrase enzyme catalyzes $CO_2$ dissolution in three steps as depicted in FIG. 4. First, a water molecule bound to the metal center of the enzyme loses its proton. That step is believed to be rate-limiting. Second, the proton exits to solution by Grotthus shuttling and the remaining zinc-bound hydroxide ($OH^-$) executes nucleophilic attack on a nearby $CO_2$ to form $HCO_3^-$. The enzyme stabilizes $CO_2$ in the vicinity of the hydroxide to facilitate that reaction. In the final step, a water replaces $HCO_3^-$ and the active site recovers its original form. The result of the enzyme catalysis reaction is enhanced solubility of $CO_2$ specifically and at fast rates. The enzyme also catalyzes the reverse reaction—dehydration of $HCO_3^-$ specifically to form $CO_2$ and water at fast rates (counter-clockwise in FIG. 4). Which reaction is favored depends on the availability of $CO_2$ compared to $HCO_3^-$ and protons in the permeation medium. For example, $CO_2$ uptake and dissolution is favored at the feeding side of the membrane where $CO_2$ concentrations are high. $HCO_3^-$ dehydration and $CO_2$ release to gas phase is favored at the collecting side of the membrane when the availability of protons and $HCO_3^-$ is high. The reaction may be catalyzed by one enzyme, or two enzymes, or more than two enzymes, or one or more other catalyst.

In the specific example of carbon dioxide as depicted in FIG. 4, the chemical reaction is catalyzed by an enzyme (En) that converts carbon dioxide into the more soluble bicarbonate ion and a proton after reaction with a metal-bound water: $CO_2 + H_2O \rightleftharpoons HCO_3^- + H^+$. The enzyme may be carbonic anhydrase (CA) with a zinc ($Zn^{2+}$) ion in the active site. The forward reaction is favored in solutions with excess $CO_2$. The reverse reaction is favored in solutions with excess $H^+$ and $HCO_3^-$.

While the object species 12 will generally move from a region of relatively higher object species concentration to a region of relatively lower object species concentration, various conditions may be controlled so that the object species is pumped from a region of lower concentration to a region of higher concentration. For example, the atmospheric pressure and/or atmospheric temperature may be increased within the region of relatively lower concentration to move the object species toward the region of relatively higher concentration. Also, the enzyme may be modified to change its catalytic behavior. The electronic environment around the metal ion enhances the acidity of the metal-bound water to a value of 6.8 in units of $pK_a$ compared to the value of 15.7 in liquid water. Thus the metal-bound water tends to lose its proton even in neutral solutions (pH=7), meaning that the enzyme favors uptake of $CO_2$ in neutral solutions. Mutations to amino acid residues surrounding the metal ion can alter the electronic environment and change the acidity of the metal-bound water, and thus change whether $CO_2$ uptake or release is favored for specific solution conditions.

As described above, the nanoporous layer 18 (e.g., the nanoporous silica) within the pores 16 may be treated so that a first portion, the portion adjacent to the high $CO_2$ concentration region 13, is hydrophilic (i.e., the hydrophilic portion 18A) while a second portion, the portion away from the high $CO_2$ concentration region and closer to the lower $CO_2$ concentration region 15, is hydrophobic (i.e., the hydrophobic portion 18B). The hydrophilic portion 18A may thus be referred to as an active layer of the nanoporous layer 18 and the hydrophobic portion 18B may be referred to as a passive layer of the nanoporous layer 18. The liquid transport medium 20 is thus drawn toward the hydrophilic portion 18A such that the hydrophobic portion 18B of the nanoporous layer 18 remains dry or dryer than the hydrophilic portion 18A. The net effect is a thinner layer of the transport medium 20. Because the transport medium 20 is thinner, resulting from the thin hydrophilic portion 18A, the transport time across the transport medium 20 is decreased as the distance across the transport medium 20 is decreased. The thickness of the hydrophilic portion 18A (i.e., the active region) may be very small as long as the nanoporous layer 18 is sufficiently thin.

Forming a modified (e.g., hydrophilic) silica layer that has a total thickness of 10 nm or less using plasma-assisted atomic layer deposition (ALD) process has been demonstrated (see Jiang et al., J. American Chemical Society, 2008). A silica layer having a thickness of less than 10 nm thick can be formed with a plasma-assisted ALD process as described below to form a nanoporous layer 18 of a membrane structure 10 to filter an object species, such as a $CO_2$ membrane structure. In addition, the thickness of the hydrophilic portion 18A, i.e., the hydrophilic "active layer" of the silica layer, may be controlled by partially modifying the exposed surfaces of the nanoporous silica to be either hydrophilic or hydrophobic, as discussed above. In an embodiment, the layer of liquid transport medium 20 within the nanoporous layer 18 (e.g. nanoporous silica) may thus have a thickness of between about 2 nm and about 10 µm, or between about 2 nm and about 10 nm.

Modification of pore surfaces such as at least a portion of surface 26 extending between first opening at first end 16A and second opening at second end 16B can include forming a film, including a continuous or discontinuous film, for example, a continuous or discontinuous thin film thereon. The film can be formed on the surface by any suitable process including atomic layer deposition. The film can comprise a peptide film. The peptide film can include a peptide thin film, such as L-alanine polypeptide thin film. Peptide film can be formed via atomic layer deposition (ALD) (see Fu et al., J. Am. Chem. Soc. 2014, 136, 15821-15824). In an example, a supporting substrate such as supporting substrate 14 was modified by an ALD process to form a peptide film thereon. The ALD can be carried out in an Angstrom-dep dual-chamber ALD system with an agitated powder ALD chamber. ALD to form a peptide thin film can be performed according to the following steps: (1) introduce Boc-L-alanine vapor to the chamber; (2) inject DCC vapor to trigger the coupling reaction between carboxyl groups in Boc-L-alanine and —$NH_2$ groups on sample surface, forming chemisorbed Boc-L-alanine; (3) purge the ALD chamber with Ar flow to remove residual Boc-L-alanine, DCC, and byproducts, leaving only a monolayer of chemisorbed Boc-L-alanine on the sample surface; (4) introduce phosphoric acid vapor to strip off Boc protective groups from the chemisorbed Boc-L-alanine, exposing —$NH_2$ groups; (5) purge the chamber with Ar to remove residual phosphoric acid and byproducts, generating a new —$NH_2$ terminated surface that is ready for another layer of chemisorption; (6) repeat the coupling and deprotection processes (steps 1-5) to obtain the desired polypeptide film thickness.

The object species 12 that is dissolved within the transport medium 20 is released therefrom on the low concentration side 15 (i.e., the collecting side) of the membrane structure 10. The release process may be catalyzed by another enzyme or the same enzyme 24 as used in step one to increase the releasing rate. The CA enzyme may be used to both catalyze the $CO_2$ dissolving step and to catalyze the $CO_2$ releasing step. During transport through the transport medium 20, it will be noted that the $CO_2$ may not remain as molecular $CO_2$.

$CO_2$ permeance and selectivity measurements were carried out at room temperature. To ensure that the liquid transport medium 20 did not dry out, a water bubble generator was used. The feed gas, including the object species 12 and the carrier gas 28, was humidified by passing the feed gas through a water bubble generator so that the feed gas carried a high concentration of water vapor. To increase the water vapor concentration, the bubble generator may be heated to increase the water vapor carrying capacity of the feed gas. The water vapor will condense inside the hydrophilic portion 18A of the nanoporous layer 18 because of, for example, capillary condensation. However, the hydrophobic portion 18B of the nanoporous layer 18 remains empty or mostly empty because little or no capillary condensation takes place. The liquideous transport medium 20 of the membrane structure 10 within the hydrophilic portion 18A of the nanoporous layer 18 thus remains very stable during the separation of the object species 12 from the feed gas 12, 28 using the membrane structure 10 as a filter. A typical $CO_2$ flux was 0.2 cc per square centimeter per minute ($cm^3/cm^2/min$) at 1 atmosphere (atm) of pressure difference for the produced membranes. The highest flux was 1.2 $cm^3/cm^2/min$ at 1 atm pressure difference. The membrane may provide a $CO_2$ flux of 0.4-2.5(10)$^6$ Barrer (1 Barrer=$10^{-10}$ $cm^3/cm^{-2}$-s-cmHg$^{-1}$ at standard temperature and pressure, STP). When argon gas was used for the measurement, no permeance was detectable after 30 minutes. The combined results indicate a high flux and a high, almost perfect selectivity of object species by this membrane. In embodiments, the ratio of $CO_2$ to argon fluxes (i.e., the selectivity of $CO_2$ compared to argon during transport) may be greater than 500:1.

For a dense ultra-thin membrane structure 10, one limiting step for the flux through the membrane structure 10 is typically the initial reaction of the object species such as a feed gas 12 into the membrane surface at the high concentration side 13 of the membrane structure 10. In many cases, the temperature of the feed gas and/or the membrane surface may be increased to catalyze the surface reaction rate. However, this heating process results in negative aspects such as increased energy consumption, high-temperature sealing of the membrane pores 16, etc. In an embodiment of the present teachings, enzymes were used to catalyze the surface reaction steps. The reaction rate may be increased by more than one hundred thousand times while maintaining the membrane structure 10 at room temperature. In addition to enzyme catalysis through the use of an enzyme 24 within the liquideous permeation medium 22, other catalyzation processes, such as photo-catalyzation, catalyzation by using catalysis, etc., may be used.

The transport medium 20, which is the selectively permeable component of the membrane structure 10, may be a thin layer of aqueous or other liquid solution. This is advantageous over traditional dense (i.e., solid) polymer membranes in both the solubility of the object species to be separated and the diffusivity for the species to travel across the membrane thickness. The permeation medium 22 of the liquid transport medium 20 in accordance with an embodiment of the present teachings may be in one or more of various liquideous forms, e.g., a liquideous form with one or more other solvents such as one or more organic solvents, or in a gelatinous (i.e., gel-like) form.

The thickness of the membrane structure 10 may be reduced by using a thinner starting nanoporous layer 18, for example, a nanoporous film, during the manufacturing process. Additionally, the thickness of the membrane structure 10 may be reduced as described above by partial modification of the nanopore surface chemistry so that only a thin layer of the nanoporous layer 18, i.e., the hydrophilic portion 18A, has the property of holding the liquid transport medium 20. In other words, a partial thickness of the supporting substrate 14 and the nanoporous layer 18 may be converted from a hydrophobic surface to a hydrophilic surface, while a partial thickness of the membrane structure remains hydrophobic, thus allowing a reduction in the thickness of the hydrophilic portion 18A (i.e., the active layer) compared to the overall thickness of the membrane structure 10. This modification may be achieved by plasma treatment as described above, or by using an ozone treatment, or using other methods or a combination of methods.

A membrane structure 10 in accordance with the present teachings may be used for separation of $CO_2$ from a gaseous medium. Membrane structures may be formed to separate other object gases, for example, molecular oxygen ($O_2$), molecular hydrogen ($H_2$), or other species including non-gaseous species such as ions.

In an embodiment, the transport medium 20, including the liquideous permeation medium 22 and the catalyst enzyme 24 may be encapsulated by another semi-permeable layer, e.g., a lipid bi-layer or another porous layer where the pore size is smaller than the pore size in the active layer. Also, this liquid transport medium 20 may be sandwiched between two porous layers to improve its mechanical property, for example a scratch resistance of the membrane structure 10 during contact with other structures. The surface chemistry of the nanoporous layer 18 may be modified using other techniques not described herein to enhance various other membrane performance characteristics.

Figure 3:
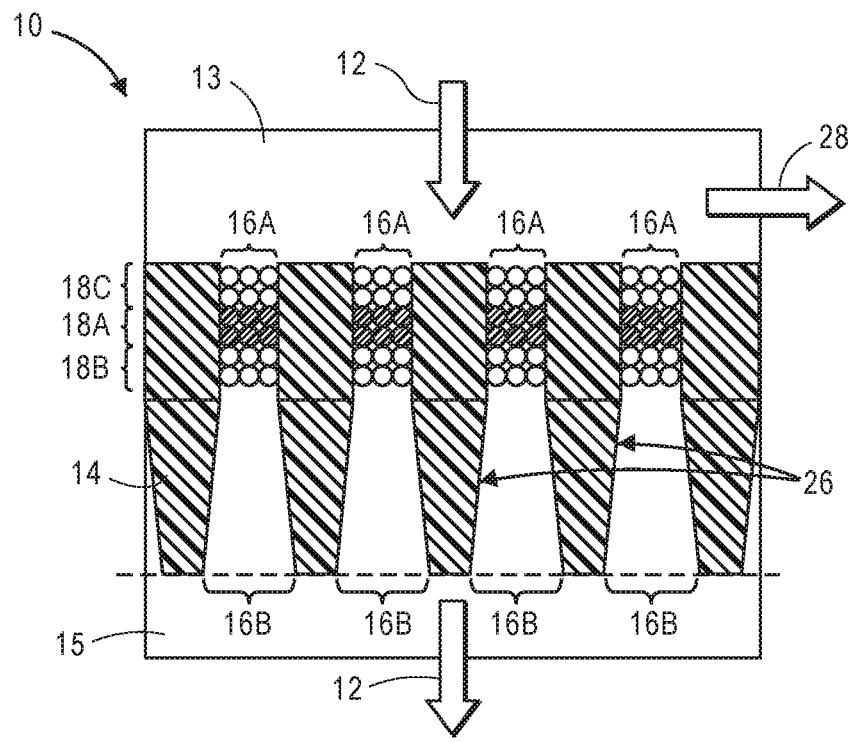
FIG. 3 is a schematic cross section depicting a membrane structure in accordance with another embodiment of the present teachings.

In another embodiment, the hydrophilic portion 18A of nanoporous layer 18 may be sandwiched between two nanoporous hydrophobic portions 18B, 18C as depicted in FIG. 3. Forming layer 18A between two nanoporous hydrophobic portions 18B, 18C may provide improved mechanical properties, for example improved scratch resistance. To form layer 18C, a structure similar to the FIG. 1 structure may be formed, then the upper portion of 18A may be treated to convert it to a hydrophobic region. For example, the upper surface of hydrophilic portion 18A in FIG. 1 may be exposed to HMDS to convert the upper part of hydrophilic portion 18A of nanoporous layer 18 to hydrophobic portion 18C as depicted in FIG. 3.

Without intending to be bound by theory, it is believed that the difference in gas concentration between the first concentration side 13 and the second concentration side 15 is a driving force for the object species to move from one side of the membrane to the other, particularly when moving the object species 12 from a region of relatively higher object species concentration to a region of relatively lower object species concentration. Considering a $CO_2$ object species, the $CO_2$ dissolving process is a reversible process in which the $CO_2$ may be dissolved into the liquid transport medium 20, and may also be released from the liquid transport medium 20. Higher $CO_2$ concentrations on the high concentration side 13 favors rapid dissolving of the object species 12 into the liquid transport medium 20 and slower release from the liquid transport medium 20 back into the higher concentration side 13. Contrarily, as the gas permeates the liquid transport medium 20, lower $CO_2$ concentrations on the low concentration side 15 favors rapid release of the object species 12 from the liquid transport medium 20 into the lower concentration side 13 and slower dissolving of the gas back into the liquid transport medium 20. This pump results in overall net $CO_2$ flow from the region of higher gas concentration 13 to the region of lower gas concentration 15. For the reversible dissolving/releasing process, a balance between the dissolving and the releasing steps will be established. At a certain $CO_2$ pressure in the feed gas 12, 28, the dissolved $CO_2$ concentration is a constant. A higher $CO_2$ pressure results in a higher concentration of $CO_2$ dissolved within the liquid transport medium 20. Therefore, the dissolved $CO_2$ has a higher concentration at the feeding side 13 (for example the high concentration side) than the collecting side 15 (for example the low concentration side). For at least this reason, the dissolved $CO_2$ will move from the high concentration side to the low concentration side through the separation layer catalyzed by the enzyme, for example CA.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

What is claimed is:

1. A membrane structure for moving a gaseous object species from a first region having an object species first concentration, through the membrane structure, to a second region having an object species second concentration different from the first concentration, comprising:
   a supporting substrate comprising a plurality of pores therethrough, each of the plurality of pores defined by a first end, a second end and a surface of the supporting substrate extending between the first end and the second end;
   a nanoporous layer within the plurality of pores, wherein the nanoporous layer comprises:
      a hydrophilic layer; and
      a hydrophobic layer; and
   a liquid transport medium within the hydrophilic layer, wherein the liquid transport medium comprises:
      a liquideous permeation medium; and
      at least one enzyme within the liquideous permeation medium, wherein the at least one enzyme is reinforced by at least one stabilizing component.

2. The membrane structure of claim 1, wherein the at least one stabilizing component comprises at least one functional group, wherein the functional group is bonded to the enzyme.

3. The membrane structure of claim 1, wherein the at least one stabilizing component is anchored to the surface of the supporting substrate.

4. The membrane structure of claim 1, wherein the at least one stabilizing component comprises a polymer.

5. The membrane structure of claim 1, wherein the at least one stabilizing component comprises glutaraldehyde.

6. The membrane structure of claim 1, wherein the at least one stabilizing component comprises a first functional group and a second functional group, wherein the first functional group is bonded to a first location of the enzyme and wherein the second functional group is bonded to a second location of the enzyme.

7. The membrane structure of claim 1, wherein the at least one enzyme is at least partially surrounded by the at least one stabilizing component.

8. The membrane structure of claim 1, wherein the liquideous permeation medium comprises water.

9. The membrane structure of claim 1, wherein the liquideous permeation medium further comprises one or more of salt, a buffer or combinations thereof.

10. The membrane structure of claim 1, wherein the enzyme comprises carbonic anhydrase.

11. The membrane structure of claim 1, wherein the at least one enzyme and the at least one stabilizing component are disposed as at least one enzyme cluster, wherein the at least one enzyme comprises at least two enzymes linked by the at least one stabilizing component.

12. The membrane structure of claim 11, wherein the at least one enzyme cluster has a size that is larger than the first end, the second end or both the first end and the second end.

13. The membrane structure of claim 11, wherein the at least one stabilizing component is further anchored to the surface.

14. The membrane structure of claim 11, wherein the at least two enzymes comprise a first enzyme and a second enzyme, wherein the at least one stabilizing component comprises a first stabilizing component and a second stabilizing component, wherein the first stabilizing component is anchored to the surface and bonded to the first enzyme, and wherein the second stabilizing component is bonded at a first functional group thereof to the first enzyme and is bonded to at a second functional group thereof to the second enzyme.

15. A method for moving an object species from a first region having an object species first concentration to a second region having an object species second concentration different from the first concentration using a membrane structure comprising a supporting substrate, wherein the method comprises:
   exposing a gas comprising the object species to a plurality of pores within a first side of the membrane structure, each of the plurality of pores defined by a first end, a second end and a surface of the supporting substrate extending between the first end and the second end;
   dissolving the object species within a liquid transport medium, wherein:
      the liquid transport medium is within a nanoporous layer that is within the plurality of pores; and
      the liquid transport medium comprises a liquideous permeation medium and at least one enzyme within the liquideous permeation medium, wherein the at least one enzyme is reinforced by at least one stabilizing component;
   after dissolving the object species within the liquid transport medium, moving the object species from the first side of the membrane structure to a second side of the membrane structure through the liquid transport medium; and
- releasing the object species from the liquid transport medium, out of the membrane structure, and into the second region.

16. The method of claim 15, wherein the at least one stabilizing component comprises at least one functional group bonded to the enzyme.

17. The method of claim 15, wherein the at least one stabilizing component is anchored to the surface of the supporting substrate.

18. The method of claim 15, wherein the at least one stabilizing component comprises a polymer.

19. The method of claim 15, wherein the at least one stabilizing component comprises glutaraldehyde.

20. The method of claim 15, wherein the at least one stabilizing component comprises a first functional group and a second functional group, wherein the first functional group is bonded to a first location of the enzyme and wherein the second functional group is bonded to a second location of the enzyme.

21. The method of claim 15, wherein the at least one enzyme and the at least one stabilizing component are disposed as at least one enzyme cluster, wherein the at least one enzyme comprises at least two enzymes linked by the at least one stabilizing component.

22. The method of claim 21, wherein the at least one enzyme cluster has a size that is larger than the first end, the second end or both the first end and the second end.

23. The method of claim 21, wherein the at least one stabilizing component is further anchored to the surface.

24. The method of claim 21, wherein the at least two enzymes comprise a first enzyme and a second enzyme, wherein the at least one stabilizing component comprises a first stabilizing component and a second stabilizing component, wherein the first stabilizing component is anchored to the surface and bonded to the first enzyme, and wherein the second stabilizing component is bonded at a first functional group thereof to the first enzyme and is bonded to at a second functional group thereof to the second enzyme.

25. A method for making a membrane structure, wherein the membrane structure is configured to move an object species from a first region having an object species first concentration at a first side of a membrane structure to a second region of having an object species second concentration different from the first concentration, the method comprising:
providing a supporting substrate comprising a plurality of pores therethrough, each of the plurality of pores defined by a first end, a second end and a surface of the supporting substrate extending between the first end and the second end;
coating the supporting substrate with a coating comprising at least one of a sol-gel, a nanoporous polymer, and a nanoporous organic-inorganic composite to bridge the plurality of pores with the coating;
drying the coating to form a hydrophobic nanoporous layer within the plurality of pores;
treating the first side of the membrane structure to modify a first portion of the hydrophobic nanoporous layer to be a hydrophilic nanoporous layer; and
exposing the nanoporous layer to a liquid transport medium wherein the liquid transport medium remains within the hydrophilic nanoporous layer and comprises a liquideous permeation medium and at least one enzyme within the liquideous permeation medium,
reinforcing the at least one enzyme with at least one stabilizing component.

26. The method of claim 25, further comprising forming the liquid transport medium, wherein the forming of the liquid transport medium comprises combining the liquideous permeation medium, the at least one enzyme and the at least one stabilizing component.

27. The method of claim 25, wherein the reinforcing of the at least one enzyme comprises bonding at least one functional group of the at least one stabilizing component on at least one functional group of the stabilizing component.

28. The method of claim 25, wherein the reinforcing further comprises anchoring the at least one stabilizing component to the surface.

29. The method of claim 25, further comprising introducing the at least one stabilizing component into the pores prior to the exposing the nanoporous layer to the liquid transport medium.

30. The method of claim 25, wherein the reinforcing comprises forming the at least one enzyme and the at least one stabilizing component as at least one enzyme cluster, wherein the at least one enzyme comprises at least two enzymes linked by the at least one stabilizing component.

31. The method of claim 30, wherein the at least one enzyme cluster has a size that is larger than the first end, the second end or both the first end and the second end.

32. The method of claim 30, wherein the at least one stabilizing component is further anchored to the surface.

33. The method of claim 30, wherein the at least two enzymes comprise a first enzyme and a second enzyme, wherein the at least one stabilizing component comprises a first stabilizing component and a second stabilizing component, wherein the first stabilizing component is anchored to the surface and bonded to the first enzyme, and wherein the second stabilizing component is bonded at a first functional group thereof to the first enzyme and is bonded to at a second functional group thereof to the second enzyme.

34. The method of claim 30, wherein the forming of the at least one enzyme and the at least one stabilizing component as at least one enzyme cluster comprises introducing the at least one stabilizing component prior to the exposing the nanoporous layer to the liquid transport medium.

35. The method of claim 25, wherein the treating the first side of the membrane structure comprises converting a first portion of the hydrophobic nanoporous layer to a hydrophilic nanoporous layer, while a second portion of the hydrophobic nanoporous layer remains hydrophobic.

36. The method of claim 25, wherein the treating comprises modifying the surface with a peptide chemistry by atomic layer deposition, chemical vapor deposition, or other surface treatment.

37. The method of claim 36, wherein the peptide chemistry comprises one or more of a single amino acid, a chain of several connected amino acids, natural amino acids, unnatural amino acids, multiple types of amino acids, or combinations thereof.

* * * * *